(12) United States Patent
Padilla-Acevedo et al.

(10) Patent No.: US 9,518,147 B2
(45) Date of Patent: Dec. 13, 2016

(54) ADDUCT COMPOSITIONS

(71) Applicant: Dow Global Technologies LLC, Midland, MI (US)

(72) Inventors: Angela I. Padilla-Acevedo, Lake Jackson, TX (US); Nathan Wilmot, Missouri City, TX (US); Rajat Duggal, Pearland, TX (US); Harshad M. Shah, Missouri City, TX (US); Kwanho Chang, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/430,651

(22) PCT Filed: Sep. 24, 2013

(86) PCT No.: PCT/US2013/061426
§ 371 (c)(1),
(2) Date: Mar. 24, 2015

(87) PCT Pub. No.: WO2014/052319
PCT Pub. Date: Apr. 3, 2014

(65) Prior Publication Data
US 2015/0259466 A1 Sep. 17, 2015

Related U.S. Application Data

(60) Provisional application No. 61/706,974, filed on Sep. 28, 2012.

(51) Int. Cl.
| | | |
|---|---|---|
| *C08G 59/14* | (2006.01) | |
| *C08G 65/26* | (2006.01) | |
| *C08G 59/24* | (2006.01) | |
| *C08G 59/06* | (2006.01) | |
| *C08G 59/18* | (2006.01) | |
| *C07D 303/02* | (2006.01) | |

(52) U.S. Cl.
CPC ........... *C08G 59/245* (2013.01); *C07D 303/02* (2013.01); *C08G 59/066* (2013.01); *C08G 59/1477* (2013.01); *C08G 59/184* (2013.01); *C08G 65/2624* (2013.01)

(58) Field of Classification Search
None
See application file for complete search history.

(56) References Cited

U.S. PATENT DOCUMENTS

| 4,689,131 A * | 8/1987 | Roue ................. C08G 18/0814 |
| | | 204/499 |
| 4,940,770 A | 7/1990 | Speranza et al. |
| 5,032,629 A * | 7/1991 | Hansen ................ C08G 59/184 |
| | | 523/414 |
| 5,241,016 A | 8/1993 | Waddill et al. |
| 2008/0293870 A1 | 11/2008 | Volle et al. |
| 2010/0285309 A1 | 11/2010 | Barriau et al. |
| 2012/0157620 A1 | 6/2012 | Nagy et al. |

FOREIGN PATENT DOCUMENTS

| EP | 0193685 | 9/1986 | |
| JP | 2007204532 | 8/2007 | |
| SU | 1199775 A1 * | 12/1985 | |
| WO | WO 2011/024014 A1 * | 3/2011 | .......... C08B 18/643 |

OTHER PUBLICATIONS

Huntsman Technical Bulletin for Jeffamine T-403 polyoxypropylene primary triamine, 2007, 2008, two pages.*
Huntsman Technical Bulletin for Jeffamine T-3000 polyoxypropylene primary triamine, 2007, 2008, 2009, two pages.*
Huntsman Technical Bulletin for Jeffamine T-5000 polyoxyethylene primary triamine, 2006, 2008, 2011, two pages.*
Soviet Union Patent No. 1,199,775 A, Mandzyuk et al., Dec. 23, 1985, English transation, 8 pages.*
Huntsman technical bulletin for Jeffamine T-403 Polyetheramine, 2007, two pages.*
Huntsman technical bulletin for Jeffamine T-3000 Polyetheramine, 2007, two pages.*
Huntsman technical bulletin for Jeffamine T-5000 Polyetheramine, 2006, two pages.*
International Search Report and Written Opinion for related PCT Application PCT/US2013/061426, received May 26, 2014 (9 pgs).

* cited by examiner

*Primary Examiner* — Robert Sellers
(74) *Attorney, Agent, or Firm* — Brooks, Cameron & Huebsch, PLLC

(57) ABSTRACT

An amine endcapped adduct composition including an amine endcapped adduct formed from a monofunctional epoxide and a polyether amine. The monofunctional epoxide and the polyether amine are combined in a molar ratio of 1.0:2.0 to 1.0:8.0 moles of epoxide functionalities to moles of polyether amine functionalities.

10 Claims, No Drawings

ADDUCT COMPOSITIONS

This application is a National Stage Application under 35 U.S.C. §371 of International Application Number PCT/US2013/061426, filed Sep. 24, 2013 and published as WO 2014/052319 on Apr. 3, 2014, which claims the benefit to U.S. Provisional Application 61/706,974, filed Sep. 28, 2012, the entire contents of which are incorporated herein by reference in its entirety.

FIELD OF DISCLOSURE

The present disclosure relates generally to adduct compositions, and more particularly to adduct compositions that may be utilized in a curable composition.

BACKGROUND

Epoxy products can be formed from an epoxy and a curing agent, which may be referred to as a hardener, which reacts with the epoxy. These two components chemically react, or "cure," to form the cured epoxy product. Upon curing an epoxy composition, including the epoxy and the hardener, forms a cross-linked network.

Compositions and epoxy products formed from those compositions can have a variety of properties. These properties can depend upon the choice of epoxy, hardener, ratio of components, reaction conditions, and/or additives, if any, present in the composition. For high mechanical stress applications, the choice of these components can help to achieve a desired result.

SUMMARY

Embodiments of the present disclosure provide an amine endcapped adduct composition. The amine endcapped adduct composition can include an amine endcapped adduct formed from a monofunctional epoxide and a polyether amine, where the monofunctional epoxide and the polyether amine are combined in a molar ratio of 1.0:2.0 to 1.0:8.0 moles of epoxide functionalities to moles of polyether amine functionalities.

Embodiments of the present disclosure provide an epoxy endcapped adduct composition. The epoxy endcapped adduct composition can include an epoxy endcapped adduct formed from the amine endcapped adduct composition and a multi-functional epoxide, where the amine endcapped adduct composition and the multi-functional epoxide are combined in a molar ratio of 1.0:2.0 to 1.0:8.0 moles of amine endcapped adduct functionalities to moles of multi-functional epoxide functionalities.

Embodiments of the present disclosure also provide a curable composition. The curable composition can include the epoxy endcapped adduct composition and a curing agent, where the epoxy endcapped adduct composition and the curing agent are combined in a molar ratio of 0.85:1.0 to 1.0:0.85 moles of epoxy endcapped adduct functionalities to moles curing agent functionalities.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION

Embodiments of the present disclosure provide an amine endcapped adduct composition. The amine endcapped adduct composition may be used to form an epoxy endcapped adduct composition, as discussed herein. The epoxy endcapped adduct composition may be utilized in curable compositions, which may be cured to form a product. Advantageously, the epoxy endcapped adduct composition has a lower viscosity via a reduced functionality, as compared to components of some other compositions. This lower viscosity can help to provide enhanced workability, as compared to other higher viscosity compositions. Additionally, products formed form the curable compositions, as disclosed herein, have desirable mechanical properties. For example, the product can maintain flexibility and/or absorb energy and elastically and/or plastically deform without fracturing. These properties can be advantageous for high mechanical stress applications, for example, coatings utilized in high traffic (e.g., maritime environments), such as marine deck coatings.

As mentioned, embodiments of the present disclosure provide an amine endcapped adduct composition including an amine endcapped adduct formed from a monofunctional epoxide and a polyether amine. Examples of the monofunctional epoxide include, but are not limited to, monofunctional aliphatic glycidyl ethers, monofunctional aromatic glycidyl ethers, or a combination thereof, among others. The monofunctional epoxide can be selected from the group consisting of alkyl $C_{12}$-$C_{14}$ glycidyl ether, butyl glycidyl ether, 2-ethylhexyl glycidyl ether, cresyl glycidyl ether, or a combination thereof.

The monofunctional epoxide can have an epoxy equivalent weight (EEW) of 100 grams to 8000 grams. EEW may be calculated as the mass in grams of epoxy, e.g., the monofunctional epoxide, containing one mole of epoxide functionalities. All individual values and subranges from and including 100 grams to 8000 grams are included herein and disclosed herein; for example, the monofunctional epoxide can have an epoxy equivalent weight with a lower limit of 100 grams, 200 grams, or 500 grams to an upper limit of 8000 grams, 7500 grams, or 7000 grams.

The polyether amine can include from 2 to 6 amine functional groups, e.g., polyether amine functionalities. For example, the polyether amine can include 2, 3, 4, 5, or 6 amine functional groups. Examples of the polyether amine include, but are not limited to, primary diamines, secondary diamines, primary triamines, secondary triamines or a combination thereof. The polyether amine can be selected from the group consisting of primary diamines and/or triamines having a polyethylene glycol or polypropylene glycol backbone; polyether amines resulting from the reaction of propylene oxide with a triol initiator, followed by amination of the terminal hydroxyl groups, among other suitable polyether amines. Examples of primary or secondary amines include, but are not limited to, those sold under the trade designator JEFFAMINE® T5000, JEFFAMINE® T3000, JEFFAMINE® D4000, JEFFAMINE® D2000, JEFFAMINE® SD2001, or a combination thereof, available from the available from Huntsman International LLC. The polyether amine can be a primary triamine, for example JEFFAMINE® T5000 (a primary triamine) available from Huntsman Corp. (amine equivalent weight=952 grams).

The polyether amine can have an amine equivalent weight (AEW) of 30 grams to 2000 grams. AEW may be calculated as the mass in grams of polyether amine containing one mole of amine functional groups. All individual values and sub-ranges from and including 30 grains to 2000 grams are included herein and disclosed herein; for example, the polyether amine can have an amine equivalent weight with a lower limit of 30 grams, 40 grams, or 50 grams to an upper limit of 2000 grams, 1750 grams, or 1500 grams.

As mentioned, the amine endcapped adduct composition includes an amine endcapped adduct formed from the monofunctional epoxide and the polyether amine. An adduct is a compound that is formed from a combination of two or more separate compounds. The combination can be a chemical reaction, such as an addition reaction. The amine endcapped adduct can be formed by combining the monofunctional epoxide and the polyether amine in a molar ratio of 1.0:2.0 to 1.0:8.0 moles of epoxide functionalities to moles of polyether amine functionalities. All individual values and subranges from and including 1.0:2.0 to 1.0:8.0 are included herein and disclosed herein; for example, the monofunctional epoxide and the polyether amine can be combined in a molar ratio of moles of epoxide functionalities to moles of polyether amine functionalities with a upper limit of 1.0:8.0, 1.0:7.8, or 1.0:7.5 to a lower limit of 1.0:2.0, 1.0:2.2, or 1.0:2.5.

The monofunctional epoxide and the polyether amine, e.g., when forming the amine endcapped adduct and/or the amine endcapped adduct composition can be heated to a temperature from 35° C. to 160° C. All individual values and subranges from and including 35° C. to 160° C. are included herein and disclosed herein; for example the monofunctional epoxide and the polyether amine can be heated to a temperature with a lower limit of 35° C., 45° C., or 55° C. to an upper limit of 160° C., 150° C., or 140° C.

The amine endcapped adduct composition may include a catalyst. The catalyst can be used to promote the reaction of the monofunctional epoxide and the polyether amine. Examples of the catalyst can include 1-methylimidazole, 2-ethyl-4-methylimidazole, 1-benzyl-2methyl imidazole, benzyldimethyl amine, benzyltriethyl ammonium chloride, or a combination thereof, among other catalysts. The catalyst can be employed in the amine endcapped adduct composition from 0.1 weight percent to 5 weight percent based on a total weight of the monofunctional epoxide and the polyether amine. All individual values and subranges from and including 0.1 weight percent to 5 weight percent are included herein and disclosed herein; for example catalyst can be employed in the amine endcapped adduct composition with a lower limit of 0.1 weight percent, 0.25 weight percent, or 0.5 weight percent to an upper limit of 5 weight percent, 4.5 weight percent, or 4.0 weight percent based on a total weight of the monofunctional epoxide and the polyether amine.

Embodiments of the present disclosure provide an epoxy endcapped adduct composition. The epoxy endcapped adduct composition can include an epoxy endcapped adduct formed from the amine endcapped adduct composition, discussed herein, and a multi-functional epoxide.

The multi-functional epoxide can have multiple epoxide functionalities, e.g., more than one epoxide functionality, per multi-functional epoxide molecule. The multi-functional epoxide can be selected from the group consisting of an aromatic epoxy, an alicyclic epoxy, an aliphatic epoxy, or a combination thereof.

Examples of the multi-functional epoxide include, but are not limited to, those sold under the trade designator D.E.R.™ 330, D.E.R.™ 331, D.E.R.™ 332, D.E.R.™ 324, D.E.R.™ 352, D.E.R.™ 354, D.E.R.™ 383, D.E.R.™ 542, D.E.R.™ 560, D.E.N.™ 431, D.E.N.™ 438, D.E.R.™ 736, D.E.R.™ 732, or a combination thereof. These multi-functional epoxides are available from The Dow Chemical Company.

Examples of aromatic epoxies include, but are not limited to, divinylarene dioxide, glycidyl ether compounds of polyphenols, such as hydroquinone, resorcinol, bisphenol A, bisphenol F, 4,4'-dihydroxybiphenyl, phenol novolac, cresol novolac, trisphenol (tris-(4-hydroxyphenyl)methane), 1,1,2,2-tetra(4-hydroxyphenyl)ethane, tetrabromobisphenol A, 2,2-bis(4-hydroxyphenyl)-1,1,1,3,3,3-hexafluoropropane, and 1,6-dihydroxynaphthalene.

Examples of alicyclic epoxies include, but are not limited to, polyglycidyl ethers of polyols having at least one alicyclic ring, or compounds including cyclohexene oxide or cyclopentene oxide obtained by epoxidizing compounds including a cyclohexene ring or cyclopentene ring with an oxidizer. Some particular examples include, but are not limited to, hydrogenated bisphenol A diglycidyl ether; 3,4-epoxycyclohexylmethyl-3,4-epoxycyclohexyl carboxylate; 3,4-epoxy-1-methylcyclohexyl-3,4-epoxy-1-methylhexane carboxylate; 6-methyl-3,4-epoxycyclohexylmethyl-6-methyl-3,4-epoxycyclohexane carboxylate; 3,4-epoxy-3-methylcyclohexylmethyl-3,4-epoxy-3-methylcyclohexane carboxylate; 3,4-epoxy-5-methylcyclohexylmethyl-3,4-epoxy-5-methylcyclohexane carboxylate; bis(3,4-epoxycyclohexylmethyl)adipate; methylene-bis(3,4-epoxycyclohexane); 2,2-bis(3,4-epoxycyclohexyl)propane; dicyclopentadiene diepoxide; ethylene-bis(3,4-epoxycyclohexane carboxylate); dioctyl epoxyhexahydrophthalate; and di-2-ethylhexyl epoxyhexahydrophthalate, 4-epoxycyclohexylmethyl 3,4-epoxycyclohexanecarboxylate, bis(3,4-epoxycyclohexyl methyl) adipate, 1,4-cyclohexanedimethanol bis(3,4-epoxycyclohexanecarboxylate), dicyclopentadiene dioxide, 3,3'-(1-methylethylidene)bis-7-oxabicyclo[4.1.0]heptane.

Examples of aliphatic epoxies include, but are not limited to, polyglycidyl ethers of aliphatic polyols or alkylene-oxide adducts thereof, polyglycidyl esters of aliphatic long-chain polybasic acids, homopolymers synthesized by vinyl-polymerizing glycidyl acrylate or glycidyl methacrylate, and copolymers synthesized by vinyl-polymerizing glycidyl acrylate or glycidyl methacrylate and other vinyl monomers. Some particular examples include, but are not limited to glycidyl ethers of polyols, such as 1,4-butanediol diglycidyl ether; 1,6-hexanediol diglycidyl ether; a triglycidyl ether of glycerin; a triglycidyl ether of trimethylol propane; a tetraglycidyl ether of sorbitol; a hexaglycidyl ether of dipentaerythritol; a diglycidyl ether of polyethylene glycol; and a diglycidyl ether of polypropylene glycol; polyglycidyl ethers of polyether polyols obtained by adding one type, or two or more types, of alkylene oxide to aliphatic polyols such as propylene glycol, trimethylol propane, and glycerin; and diglycidyl esters of aliphatic long-chain dibasic acids.

The multi-functional epoxide can have an epoxide equivalent weight of 50 grams to 4000 grams. All individual values and subranges from and including 50 grams to 4000 grams are included herein and disclosed herein; for example, the multi-functional epoxide can have an epoxy equivalent weight with a lower limit of 50 grams, 75 grams, or 100 grams to an upper limit of 4000 grams, 3750 grams, or 3500 grams.

As mentioned, the epoxy endcapped adduct composition includes an epoxy endcapped adduct formed from the amine endcapped adduct composition, as discussed herein, and the multi-functional epoxide. The epoxy endcapped adduct can be formed by combining the amine endcapped adduct composition and the multi-functional epoxide in a molar ratio of 1.0:2.0 to 1.0:8.0 moles of amine endcapped adduct functionalities to moles multi-functional epoxide functionalities. All individual values and subranges from and including 1.0:2.0 to 1.0:8.0 are included herein and disclosed herein; for example, the amine endcapped adduct composition and the multi-functional epoxide can be combined in a molar ratio of moles of amine endcapped adduct functionalities to moles multi-functional epoxide functionalities with a upper limit of 1.0:8.0, 1.0:7.8, or 1.0:7.5 to a lower limit of 1.0:2.0, 1.0:2.2, or 1.0:2.5.

For one or more embodiments, the epoxy endcapped adduct composition may include a catalyst. The catalyst can be used to promote the reaction of the amine endcapped adduct composition, as discussed herein, and the multi-functional epoxide. Examples of the catalyst include 1-methylimidazole, 2-ethyl-4-methylimidazole, 1-benzyl-2methyl imidazole, benzyldimethyl amine, benzyltriethyl ammonium chloride, and combinations thereof, among other catalysts. The catalyst can be employed in the amine endcapped adduct composition in a range from 0.1 weight percent to 5 weight percent based on a total weight of the amine endcapped adduct composition and the multi-functional epoxide. All individual values and subranges from and including 0.1 weight percent to 5 weight percent are included herein and disclosed herein; for example catalyst can be employed in the amine endcapped adduct composition in a range with a lower limit of 0.1 weight percent, 0.25 weight percent, or 0.5 weight percent to an upper limit of 5 weight percent, 4.5 weight percent, or 4.0 weight percent based on a total weight of the amine endcapped adduct composition and the multi-functional epoxide.

The epoxy endcapped adduct composition can have a viscosity at 25° C. from 5000 centipoise to 50000 centipoise. Viscosity is obtained from measurement on parallel plate set-up on a rheometer using a shear rate of 1 s$^{-1}$ and temperature ramp (rate 3° C./min) from room temperature to 80° C. according to ASTM D 4065-94. All individual values and subranges from and including 5000 centipoise to 50000 centipoise are included herein and disclosed herein; for example epoxy endcapped adduct composition can have a viscosity at 25° C. in a range with a lower limit of 5000 centipoise, 7500 centipoise, or 10000 centipoise to an upper limit of 50000 centipoise, 45000 centipoise, or 40000 centipoise. For example, the epoxy endcapped adduct composition can have a viscosity at 25° C. in a range of from 5000 centipoise to 50000 centipoise, 25000 centipoise to 50000 centipoise, 10000 centipoise to 45000 centipoise, and/or 15000 centipoise to 40000 centipoise, among others.

Embodiments of the present disclosure provide curable compositions. The curable composition can include the epoxy endcapped adduct composition, as discussed herein, and a curing agent. The curing agent can be selected from the group consisting of an anhydride, an amine, a phenolic, or a combination thereof.

An anhydride is a compound having an anhydride group, e.g., two acyl groups bonded to the same oxygen atom. The anhydride can be symmetric or mixed. Symmetric anhydrides have identical acyl groups. Mixed anhydrides have different acyl groups. The anhydride can be selected from the group consisting of hexahydrophthalic anhydride, methyltetrahydrophthalic anhydride, methylhexahydrophthalic anhydride, methylnadic anhydride, methylbutenyltetrahydrophthalic anhydride, or a combination thereof.

Amines include compounds that contain an N—H moiety, e.g., primary amines and secondary amines. The amine can be selected from the group consisting of aliphatic polyamines, arylaliphatic polyamines, cycloaliphatic polyamines, aromatic polyamines, heterocyclic polyamines, polyalkoxy polyamines, dicyandiamide and derivatives thereof, aminoamides, amidines, ketimines, ethanolamines, or a combination thereof.

Examples of aliphatic polyamines include, but are not limited to, ethylenediamine, diethylenetriamine, triethylenetetramine, trimethyl hexane diamine, hexamethylenediamine, N-(2-aminoethyl)-1,3-propanediamine, N,N'-1,2-ethanediylbis-1,3-propanediamine, dipropylenetriamine, or a combination thereof.

Examples of arylaliphatic polyamines include, but are not limited to, m-xylylenediamine, and p-xylylenediamine. Examples of cycloaliphatic polyamines include, but are not limited to, 1,3-bisaminocyclohexane, isophorone diamine, and 4,4'-methylenebiscyclohexaneamine. Examples of aromatic polyamines include, but are not limited to, m-phenylenediamine, diaminodiphenylmethane, and diaminodiphenylsulfone. Examples of heterocyclic polyamines include, but are not limited to, N-aminoethylpiperazine, 3,9-bis(3-aminopropyl) 2,4,8,10-tetraoxaspiro(5,5)undecane, or a combination thereof.

Examples of polyalkoxy polyamines include, but are not limited to, 4,7-dioxadecane-1,10-diamine; 1-propanamine; (2,1-ethanediyloxy)-bis-(diaminopropylated diethylene glycol) (ANCAMINE® 1922A); poly(oxy(methyl-1,2-ethanediyl)), alpha-(2-aminomethylethyl)omega-(2-aminomethylethoxy) (JEFFAMINE® D-230, D-400); triethyleneglycoldiamine; and oligomers (JEFFAMINE® XTJ-504, JEFFAMINE® XTJ-512); poly(oxy(methyl-1,2-ethanediyl)), alpha,alpha'-(oxydi-2,1-etha nediyl)bis (omega-(aminomethylethoxy)) (JEFFAMINE® XTJ-511); bis(3-aminopropyl)polytetrahydrofuran 350; bis(3-aminopropyl)polytetrahydrofuran 750; poly(oxy(methyl-1,2-ethanediyl)); α-hydro-ω-(2-aminomethylethoxy) ether with 2-ethyl-2-(hydroxymethyl)-1,3-propanediol (JEFFAMINE® T-403); diaminopropyl dipropylene glycol; or a combination thereof.

Examples of dicyandiamide derivatives include, but are not limited to, guanazole, phenyl guanazole, cyanoureas, or a combination thereof.

Examples of aminoamides include, but are not limited to, amides formed by reaction of the above aliphatic polyamines with a stoichiometric deficiency of anhydrides and carboxylic acids, as described in U.S. Pat. No. 4,269,742.

Examples of amidines include, but are not limited to, carboxamidines, sulfinamidines, phosphinamidines, or a combination thereof.

Examples of ketimines include compounds having the structure $(R^2)_2C=NR^3$, where each $R^2$ is an alkyl group and $R^3$ is an alkyl group or hydrogen, or a combination thereof.

Examples of ethanolamines include, but are not limited to, monoethanolamine, diethanolamine, triethanolamine, or a combination thereof.

Examples of phenolics include, but are not limited to, bisphenols, novolacs, and resoles that can be derived from phenol and/or a phenol derivative, or a combination thereof.

Embodiments of the present disclosure provide that the epoxy endcapped adduct composition, as discussed herein, and the curing agent can be combined in a molar ratio of 0.85:1.0 to 1.0:0.85 moles of epoxy endcapped adduct functionalities to moles curing agent functionalities. The curing agent functionalities includes functional groups of the curing agent that are capable of opening an epoxy ring, such as amine functional groups, anhydride functional groups, and hydroxyl functional groups. All individual values and subranges from and including 0.85:1.0 to 1.0:0.85 are included herein and disclosed herein; for example, the epoxy endcapped adduct composition and the curing agent can be combined in a molar ratio of moles of epoxy endcapped adduct functionalities to moles curing agent functionalities with a upper limit of 0.85:1.0, 0.87:1.0, or 0.90:1.0 to a lower limit of 1.0:0.85, 1.0:0.87, or 1.0:0.90.

For one or more embodiments, the curable composition may include a catalyst. The catalyst can be used to promote the reaction of the epoxy endcapped adduct composition and the curing agent. Examples of the catalyst include 1-methylimidazole, 2-ethyl-4-methylimidazole, 1-benzyl-2methyl imidazole, benzyldimethyl amine, benzyltriethyl ammonium chloride, or a combination thereof, among other catalysts. The catalyst can be employed in the curable composition in a range from 0.1 weight percent to 5 weight percent based on a total weight of the epoxy endcapped adduct composition and curing agent. All individual values and subranges from and including 0.1 weight percent to 5 weight percent are included herein and disclosed herein; for example catalyst can be employed in the amine endcapped adduct composition with a lower limit of 0.1 weight percent, 0.25 weight percent, or 0.5 weight percent to an upper limit of 5 weight percent, 4.5 weight percent, or 4.0 weight percent based on a total weight of the epoxy endcapped adduct composition and curing agent.

The curable composition may include an additive. Examples of additives include, but are not limited to, nonreactive and reactive diluents; fibers; fillers; aggregates; pigments; viscosity reducing agents; dyes; coloring agents; thixotropic agents; photo initiators; latent photo initiators; inhibitors; flow modifiers; accelerators; surfactants; adhesion promoters; fluidity control agents; stabilizers; ion scavengers; UV stabilizers; fire retardants; toughening agents (e.g., anhydride hardeners); wetting agents; mold release agents; coupling agents; tackifying agents, or a combination thereof. For various applications differing amounts of the additive may be employed.

The curable compositions, as disclosed herein, may be cured to form a product. For example, the curable compositions may be cured to form an elastomer, among other products. The product may be useful for a number of applications, such as flexible marine coating applications, among others.

For one or more embodiments the curable composition can be cured at a cure temperature from 0° C. to 250° C. All individual values and subranges from and including 0° C. to 250° C. are included herein and disclosed herein; for example the curable composition can be cured at a cure temperature with a lower limit of 0° C., 5° C., or 10° C. to an upper limit of 250° C., 225° C., or 200° C.

For one or more embodiments the curable composition can be cured to obtain the product for a time interval from 0.25 hours to 48 hours. All individual values and subranges from and including 0.25 hours to 48 hours are included herein and disclosed herein; for example the curable composition can be cured to obtain the product for a time interval with a lower limit of 0.25 hours, 0.5 hours, or 1.0 hours to an upper limit of 48 hours, 36 hours, or 24 hours.

The curable composition can be cured in a step wise process, where the cure temperature changes during the course of the curing process. For example, the curable composition can be cured using a cure temperature of 100° C. for a first time interval, then a cure temperature of 150° C. for a second time interval, and then a cure temperature of 200° C. for a third time interval.

As mentioned, the product may be used in a variety of applications. For some applications, it may be desirable that the product has a tensile strength in a range of 3 MPa to 5 MPa. For some applications, it may be desirable that the product has a percent elongation in a range from 150 percent to 350 percent. Use ASTM D-1708 for the method for tensile analysis.

For one or more embodiments the product may have a microphase separated morphology. For example, the molecular weight of the epoxy endcapped adduct composition can have a value, e.g., be low enough, such that a homogeneous mixture with the curing agent can be formed before cure, but induce phase separation as the curable composition cures. The presence of two or more glass transition temperatures for the product can indicate microphase separated morphology. The microphase separated morphology can help to provide mechanical properties (e.g., toughness and/or flexibility) of the product that are desirable for some applications. For some applications it may be desirable to have a glass transition temperature that is sufficiently high to meet high temperature applications. For example, the product can have a glass transition temperature (e.g., the highest glass transition temperature of multiple glass transition temperatures) in a range such temperatures in a range from 20° C. to 170° C. All individual values and subranges from and including 20° C. to 170° C. are included herein and disclosed herein; for example the product can have a glass transition temperature in a range with a lower limit of 20° C., 21° C., or 23° C. to an upper limit of 170° C., 165° C., or 160° C. The glass transition temperature can be measured according to ASTM E1269 Standard Test Method for determining specific heat capacity and ASTM E1356-08 standard test method for assignment of the glass transitions temperatures by differential scanning calorimetry.

EXAMPLES

In the Examples, various terms and designations for materials were used including, for example, the following: polyether amine (JEFFAMINE® T-5000, available from Huntsman International LLC), monofunctional epoxide (HELOXY Modifier 8™, alkyl $C_{12}$-$C_{14}$ glycidyl ether, available from Sigma-Aldrich), multi-functional epoxide (D.E.R.™ 383, diglycidyl ether of bisphenol A, available from The Dow Chemical Company), curing agent (monoethanolamine, available from Sigma Aldrich).

Example 1

Amine Endcapped Adduct Composition

Example 1, an amine endcapped adduct composition, was prepared as follows. JEFFAMINE® T-5000 (162 grams, 0.170 mole) and HELOXY Modifier 8™ (27 grams, 0.096 mole) were added to a four-necked container. The contents of the container were heated to and maintained at 120° C. while stirring for 5 hours to provide Example 1. Proton and NMR spectroscopy was utilized to determine that Example 1 had been formed. Example 1 was cooled to approximately 72° C.

Example 2

Epoxy Endcapped Adduct Composition

Example 2, an epoxy endcapped adduct composition, was prepared as follows. D.E.R.™ 383 (79 grams) was added dropwise over 30 minutes while stirring to the container having Example 1, as prepared above. The contents of the container were heated to and maintained at 120° C. under nitrogen while stirring for 4 hours to provide Example 2. Epoxy equivalent molecular weight titration was used to determine Example 2 had been formed. Example 2 had a viscosity at 25° C. of 16,400 centipoise. Viscosity was tested using parallel plate fixtures at 25° C. on a TA Instruments ARES rheometer. A 40 mm top and 50 mm bottom plate were installed on the rheometer to test the samples. The gap was set at 1.000 mm and all samples were run at a shear rate of 10 1/s using the max torque, 200 g-cm transducer.

Example 3

Curable Composition

Example 3, a curable composition, was prepared as follows. Example 2 (25 grams), monoethanolamine (1.04 grams), and DMP 30 (0.78 grams) were added to a container to provide Example 3.

Example 4

Product

Example 4, a product formed by curing Example 3, was prepared as follows. The contents of the container including Example 3 were mixed for 30 seconds at 800 rotations per minute, and then for 1 minute at 2350 rotations per minute. The contents of the container were poured into a mold having a 6.5"×6.5"×0.05" square window spacer positioned between two Duofoil aluminum sheets supported with outer steel plates. The filled mold was placed in an oven (50° C.) for 16 hours to provide Example 4.

Properties of Example 4 were determined by ASTM D1708, ASTM E1229, ASTM D2240, and Differential Scanning calorimetry. The Differential Scanning calorimetry utilized a DCS Q2000 machine and a temperature ramp at 10° C./min from −90° C. to 200° C. The properties are reported in Table 1.

TABLE 1

| | Tensile strength (MPa) | Elongation (percent) | Shore A hardness | First glass transition temperature (° C.) | Second glass transition temperature (° C.) |
|---|---|---|---|---|---|
| Example 4 | 3.8 | 290 | 48 | −47 | 91 |

The data in Table 1 shows that Example 4 has a tensile strength of 550 pounds per square inch and a percent elongation of 290 percent, indicating that Example 4 has properties desirable for some applications. Additionally, determination of the two glass transition temperatures indicates that Example 4 has microphase separated morphology.

What is claimed:

1. An amine endcapped adduct composition comprising:
   an amine endcapped adduct formed from a monofunctional epoxide and a polyether primary triamine having a polyethylene glycol backbone, wherein the monofunctional epoxide and the polyether amine are combined in a molar ratio of 1.0:2.0 to 1.0:8.0 moles of epoxide functionalities to moles of polyether amine functionalities.

2. The amine endcapped adduct composition of claim 1, wherein the monofunctional epoxide has an epoxide equivalent weight of 100 grams to 8000 grams.

3. The amine endcapped adduct composition of claim 1, wherein the polyether amine has an amine equivalent weight of 30 grams to 2000 grams.

4. The amine endcapped adduct composition of claim 1, wherein the monofunctional epoxide is selected from the group consisting of monofunctional aliphatic glycidyl ethers, monofunctional aromatic glycidyl ethers, or a combination thereof.

5. An epoxy endcapped adduct composition comprising:
   an epoxy endcapped adduct formed from the amine endcapped adduct composition of claim 1 and a multi-functional epoxide, wherein the amine endcapped adduct composition and the multi-functional epoxide are combined in a molar ratio of 1.0:2.0 to 1.0:8.0 moles of amine endcapped adduct functionalities to moles multi-functional epoxide functionalities, wherein the epoxy endcapped adduct composition has a viscosity at 25° C. of 5000 centipoise to 50000 centipoise.

6. The epoxy endcapped adduct composition of claim 1, wherein the multi-functional epoxide has an epoxide equivalent weight of 50 grams to 4000 grams.

7. The epoxy endcapped adduct composition of claim 5, wherein the multi-functional epoxide is selected from the group consisting of an aromatic epoxy, an alicyclic epoxy, an aliphatic epoxy, or a combination thereof.

8. A curable composition comprising:
   the epoxy endcapped adduct composition of claim 5 and a curing agent, wherein the epoxy endcapped adduct composition and the curing agent are combined in a molar ratio of 0.85:1.0 to 1.0:0.85 moles of epoxy endcapped adduct functionalities to moles curing agent functionalities.

9. The curable composition of claim 8, wherein the curing agent selected from the group consisting of an anhydride, an amine, a phenolic, or a combination thereof.

10. A product formed by curing the curable composition of claim 8.

* * * * *